(12) United States Patent
Kim et al.

(10) Patent No.: US 11,666,458 B2
(45) Date of Patent: Jun. 6, 2023

(54) TWO-DIMENSIONAL MEDICAL IMAGE-BASED SPINAL SURGERY PLANNING APPARATUS AND METHOD

(71) Applicant: CUREXO, INC., Seoul (KR)

(72) Inventors: Hong Ho Kim, Seoul (KR); Sung Teac Hwang, Seoul (KR)

(73) Assignee: CUREXO, INC., Seoul (KR)

( * ) Notice: Subject to any disclaimer, the term of this patent is extended or adjusted under 35 U.S.C. 154(b) by 0 days.

(21) Appl. No.: 17/917,166

(22) PCT Filed: Apr. 1, 2021

(86) PCT No.: PCT/KR2021/004099
§ 371 (c)(1),
(2) Date: Oct. 5, 2022

(87) PCT Pub. No.: WO2021/206372
PCT Pub. Date: Oct. 14, 2021

(65) Prior Publication Data
US 2023/0127917 A1   Apr. 27, 2023

(30) Foreign Application Priority Data

Apr. 6, 2020 (KR) .................. 10-2020-0041732

(51) Int. Cl.
*A61F 2/46* (2006.01)
*G06T 17/00* (2006.01)
(Continued)

(52) U.S. Cl.
CPC ............ *A61F 2/4611* (2013.01); *A61B 34/10* (2016.02); *G06T 7/30* (2017.01); *G06T 7/70* (2017.01);
(Continued)

(58) Field of Classification Search
CPC .............................. A61B 34/10; A61F 2/4611
See application file for complete search history.

(56) References Cited

U.S. PATENT DOCUMENTS

2005/0192575 A1   9/2005   Pacheco

FOREIGN PATENT DOCUMENTS

| KR | 10-2005-0061339 A | 6/2005 |
|---|---|---|
| KR | 10-2007-0045023 A | 5/2007 |

(Continued)

OTHER PUBLICATIONS

Stryker, "SpineMap 3D User Manual", 2010.

*Primary Examiner* — Andrew Yang
(74) *Attorney, Agent, or Firm* — Bridgeway IP Law Group, PLLC; Jihun Kim (57) ABSTRACT

Proposed are an apparatus and method for spinal surgery planning, the spinal surgery planning method including: acquiring a two-dimensional (2D) spinal image of a patient through a medical imaging apparatus; calculating a registration relationship between coordinates in an image space and coordinates in a surgical space by registering the image space for the spinal image and the surgical space where spinal surgery is performed on the patient; generating a virtual three-dimensional (3D) figure in the surgical space; projecting the 3D figure onto the spinal image based on the registration relationship; adjusting the 3D figure so that the 3D figure can correspond to a predetermined landmark on the spinal image; and setting an insertion position and insertion path of a spinal prosthesis based on the spinal image and the 3D figure.

14 Claims, 9 Drawing Sheets

(51) Int. Cl.
*G06T 7/30* (2017.01)
*A61B 34/10* (2016.01)
*G06T 7/70* (2017.01)

(52) U.S. Cl.
CPC ........ *G06T 17/00* (2013.01); *A61B 2034/105* (2016.02); *A61B 2034/107* (2016.02); *G06T 2207/30012* (2013.01)

(56) References Cited

FOREIGN PATENT DOCUMENTS

| | | |
|---|---|---|
| KR | 10-2009-0041649 A | 4/2009 |
| KR | 10-2009-0041654 A | 4/2009 |
| KR | 10-1264198 B1 | 5/2013 |
| KR | 10-2019-0096575 A | 8/2019 |
| KR | 10-2203544 B1 | 1/2021 |

TWO-DIMENSIONAL MEDICAL IMAGE-BASED SPINAL SURGERY PLANNING APPARATUS AND METHOD

TECHNICAL FIELD

The disclosure relates to an apparatus and method for planning spinal surgery, and more particularly to an apparatus and method for taking planning for navigation surgery or robotic surgery based on a two-dimensional (2D) spine medical image.

BACKGROUND ART

For spinal surgery using a navigation system or a surgical robot, a planning step is carried out for making a surgical plan based on a patient's medical image. For example, pedicle screw fixation surgery, in which a pedicle screw is inserted in and fixed to a vertebra body through a pedicle, is preceded by procedures of determining the length, diameter, etc., of the pedicle screw suitably according to patients and surgical sites, and making a plan for an insertion position and an insertion path.

When the planning is taken for the pedicle screw fixation surgery, an axial view of a spine is the most advantageous. Thus, according to the related art, a preoperative computed tomography (CT) axial image is provided to an operator, so that preoperative planning can be carried out based on the axial image.

A conventional planning method based on such a CT image has an advantage in that the planning can be performed on the axial image, but a disadvantage in that long-time exposure to radiation during a CT scan is harmful to a human body. In particular, in the case of the spinal surgery, a mobile C-arm or the like imaging device is used for taking an image even during an actual surgical process in order to verify in real time whether the surgery follows the surgical plan or navigate a surgical tool, thereby exacerbating problems with radiation exposure.

Further, it is necessary to register the preoperatively planned CT image to the image taken during the surgery by the C-arm or the like, which is not only cumbersome because the registration needs to be performed again whenever a patient or an imaging device moves but also causes a problem of delaying a surgical procedure. In addition, the registration between a two-dimensional (2D) image and a three-dimensional (3D) image requires a high level of registration technology, and it is very technically difficult to perform the registration with high accuracy according to the quality of images. Besides, due to the nature of the spine, a relative spinal relationship between a preoperative image and an intraoperative image is largely varied depending on a patient's poses, and it is therefore cumbersome to repeat the registration many times for each spine which will undergo a surgical operation.

Therefore, if the planning is taken based on a C-arm image or the like 2D medical image, the radiation exposure due to the CT scan is reduced and the registration between the 2D image and the 3D image is not required, thereby solving the foregoing problems. However, it is practically difficult to use the 2D medical image as the basis for the planning because the axial view is not known with the 2D medical image.

DISCLOSURE

Technical Problem

The disclosure is conceived to solve the foregoing problems with the conventional spinal surgery planning technology, and an aspect of the disclosure is to provide an apparatus and method for taking planning for spinal surgery based on a two-dimensional (2D) medical image such as a C-arm image.

Technical Solution

The aspect of the disclosure may be achieved by a spinal surgery planning method including: acquiring a two-dimensional (2D) spinal image of a patient through a medical imaging apparatus; calculating a registration relationship between coordinates in an image space and coordinates in a surgical space by registering the image space for the spinal image and the surgical space where spinal surgery is performed on the patient; generating a virtual three-dimensional (3D) figure in the surgical space; projecting the 3D figure onto the spinal image based on the registration relationship; adjusting the 3D figure so that the 3D figure can correspond to a predetermined landmark on the spinal image; and setting an insertion position and insertion path of a spinal prosthesis based on the spinal image and the 3D figure.

Here, the adjusting the 3D figure may include adjusting at least one of the shape, size and position of the 3D figure based on a user input for the 3D figure projected on the spinal image.

Meanwhile, the setting the insertion position and path of the spinal prostheses may be based on a plurality of spinal images respectively corresponding to different view directions.

Further, the plurality of spinal images respectively corresponding to different view directions may include an anterior-posterior (AP) image and a lateral-lateral (LL) image.

In addition, the setting the insertion position and path of the spinal prostheses may include setting the insertion position and path of the spinal prosthesis based on a user input using a user input unit.

Further, the adjusting the 3D figure may include adjusting the 3D figure so that a boundary of a figure formed by projecting the 3D figure on the spinal image can correspond to a boundary of a vertebral body on the spinal image.

Here, the 3D figure may have a column shape.

Further, the adjusting the 3D figure may include adjusting the 3D figure so that a first line on a lateral side of the column shape, perpendicular to a first axis on a base of the column shape passing through the center of the base, can be aligned with a center line of a spinous process on the spinal image.

Meanwhile, the spinal surgery planning method may further include setting a reference point as a reference for inserting the spinal prosthesis on the spinal image, wherein the setting the insertion position and path of the spinal prosthesis may include limiting an allowable range of the insertion position or insertion path of the spinal prosthesis based on the reference point.

Further, the generating the 3D figure may include detecting a position of a vertebra body on the spinal image, and generating the 3D figure at the detected position corresponding to the vertebra body.

In addition, the generating the 3D figure may include generating the 3D figure corresponding to characteristics of a vertebra body recognized in the spinal image, based on a library where at least one property among the size, shape and height of the 3D figure is defined according to the characteristics of the vertebra body.

Besides, the aspect of the disclosure may be achieved by a spinal surgery planning apparatus including: a memory configured to store a patient's 2D spinal image taken by a medical imaging apparatus; a registrator configured to calculate a registration relationship between coordinates in an image space and coordinates in a surgical space by registering the image space for the spinal image and the surgical space where spinal surgery is performed on the patient; a figure generator configured to generate a virtual 3D figure in the surgical space and project the 3D figure onto the spinal image based on the registration relationship; a figure adjuster configured to adjust the 3D figure so that the 3D figure can correspond to a predetermined landmark on the spinal image; and a planner configured to set an insertion position and insertion path of a spinal prosthesis based on the spinal image and the 3D figure.

Here, the spinal surgery planning apparatus may further include a display configured to display the spinal image and the 3D figure projected onto the spinal image.

Further, the spinal surgery planning apparatus may further include a 3D view generator configured to generate a 3D image for the 3D figure based on the registration relationship, wherein the planner controls a change in the spinal prosthesis on one of the spinal image and the 3D image to be reflected in each other based on the registration relationship, thereby promoting convenience for a user.

Advantageous Effects

According to the disclosure, planning is performed based on a two-dimensional (2D) medical image, thereby reducing radiation exposure due to a conventional computed tomography (CT) scan. Further, a process for registration with a three-dimensional (3D) image is omittable, thereby increasing convenience for procedures.

Besides, according to the disclosure, a three-dimensional (3D) view image for grasping a position relationship between a vertebra body and a pedicle screw at a point of view as desired by a user is generated and provided while carrying out planning based on a 2D medical image, thereby effectively replacing a CT image and guaranteeing the accuracy of navigation surgery and robotic surgery.

BEST MODE

Below, specific embodiments of the disclosure will be described with reference to the accompanying drawings. However, detailed descriptions about publicly-known functions or configurations, which may obscure the gist of the disclosure, will be omitted from the following descriptions and the accompanying drawings. It is noted that like numerals refer to like elements throughout if possible.

Figure 1:
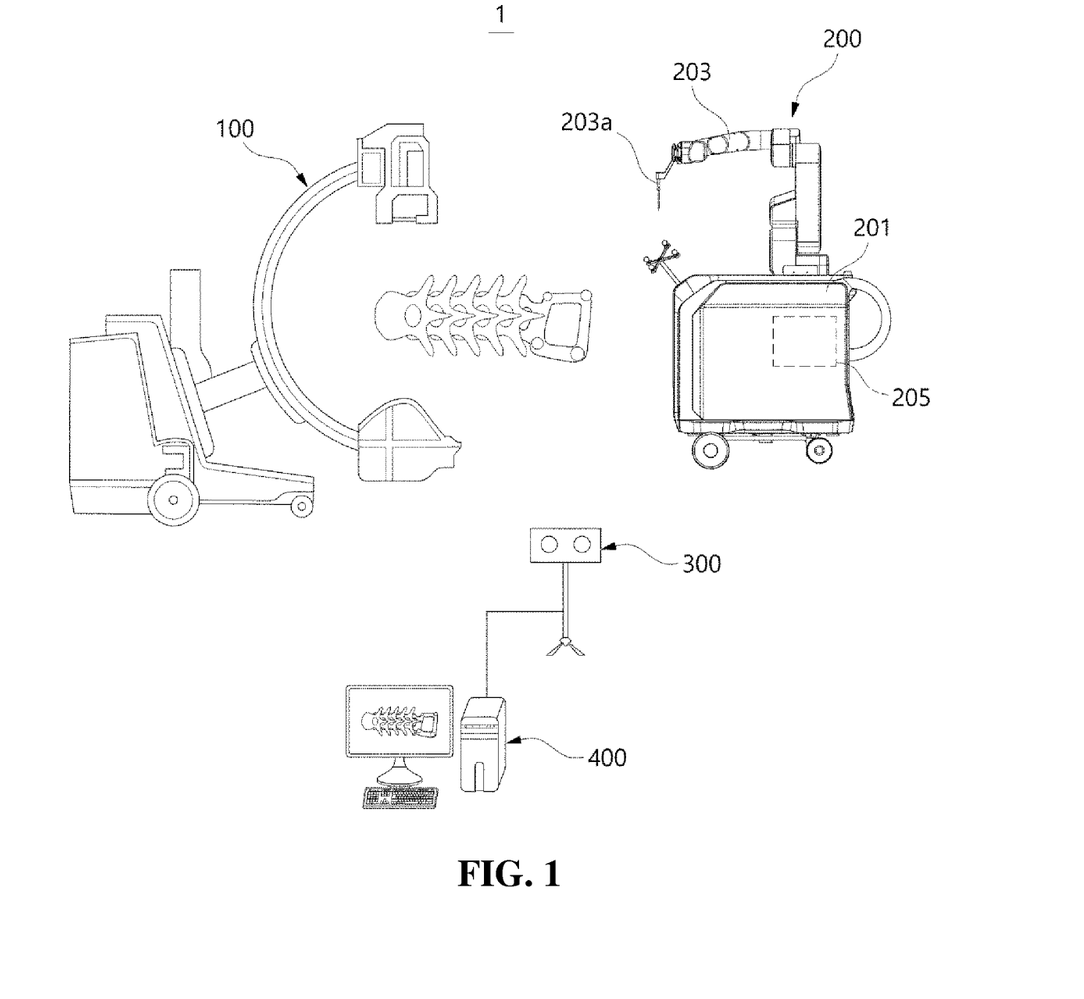
FIG. 1 is a diagram schematically showing a spinal surgery system with a spinal surgery planning apparatus according to an embodiment of the disclosure.

FIG. 1 is a diagram schematically showing a spinal surgery system with a spinal surgery planning apparatus according to an embodiment of the disclosure.

Referring to FIG. 1, a spinal surgery system 1 placed in an operating room includes a medical imaging apparatus 100, a surgical robot 200, a tracking apparatus 300, and a spinal surgery planning apparatus 400.

The medical imaging apparatus 100 refers to an apparatus for taking a spinal image of a patient, and FIG. 1 illustrates a C-arm as an example of the medical imaging apparatus 100. For reference, the C-arm refers to an apparatus for taking a two-dimensional (2D) image through an X-ray source and a detector provided at both ends of a 'C'-shaped frame. However, the C-arm is merely an example of the medical imaging apparatus 100, and other apparatuses capable of taking a 2D image by irradiating X-rays or the like to a human body may also be used as the medical imaging apparatus 100.

The medical imaging apparatus 100 may obtain a plurality of medical images at various viewpoints, i.e., viewed from different directions or angles, while moving the source and the detector with respect to a patient through the rotation or translation of the frame. For example, an anterior-posterior (AP) image may be obtained by irradiating X-rays from the anterior side of a human body to the posterior side, and a lateral-lateral (LL) image may be obtained by irradiating X-rays from the lateral side to the lateral side.

The surgical robot 200 refers to a robot that carries out pedicle screw insertion or the like spinal surgery, and includes a robot base 201, a robot arm 203, and a robot controller 205 for controlling operations of the robot arm 203, in which various surgical tools 203a such as a reaming tool and a driver may be coupled to the end, i.e., the end-effector of the robot arm 203. Further, the surgical robot 200 may be provided with a force/torque sensor (not shown) that can detect force and torque applied to the end-effector. The base 201 and the surgical tool 203a of the surgical robot 200 may be provided with optical markers that can be used as references for tracking the position of the surgical robot 200 during surgery.

For reference, FIG. 1 illustrates that the surgical robot 200 is used to perform the spinal surgery, but a medical navigation system may be used instead of the surgical robot 200.

The tracking apparatus 300 is configured to track the positions and poses of the optical markers fixed to a surgical site and the surgical robot 200, and may be implemented as an optical tracking system (OTS). For reference, the OTS refers to a system in which two infrared cameras are used to track the markers and the distances of the markers are converted by triangulation, thereby tracking a position and a pose in a three-dimensional (3D) space in real time. A commercially available OTS not only provides the distance, orientation, and height to the optical markers, but also has a function of transformation between optical marker coordinate systems. The tracking principle of such an OTS is well known, and therefore detailed descriptions thereof will be omitted for simplicity.

The spinal surgery planning apparatus 400 identifies the lengths, diameters, sizes, etc. of various spinal prostheses to be inserted and fixed during spinal surgery, such as a pedicle screw or the like, for the spinal surgery using the navigation system or the surgical robot, and provides a computer simulation environment where a surgical plan can be made for the position, direction, angle, path, depth, etc. of the insertion.

The spinal surgery planning apparatus 400 may include a processor and a display. FIG. 1 illustrates that the spinal surgery planning apparatus 400 is implemented as an additional apparatus physically separated from the surgical robot 200. However, as necessary, the processor of the spinal surgery planning apparatus 400 may be placed inside the surgical robot 200, and the display may be connected to the tracking apparatus 300. In this case, the processor and the display can transmit and receive various pieces of information through a communication module.

Figure 2:
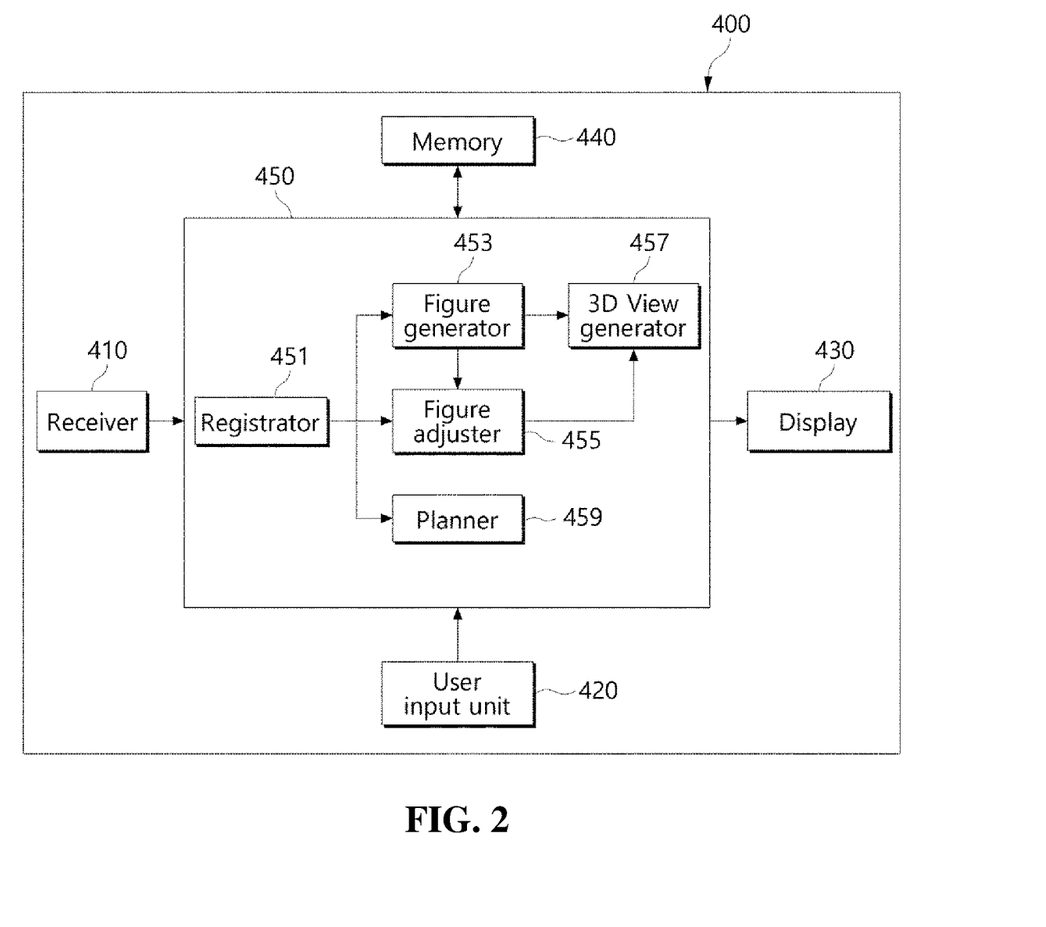
FIG. 2 is a block diagram of a spinal surgery planning apparatus according to an embodiment of the disclosure.

FIG. 2 is a block diagram showing the detailed configurations of the spinal surgery planning apparatus 400 according to an embodiment of the disclosure. Referring to FIG. 2, the spinal surgery planning apparatus 400 according to the embodiment of the disclosure includes a receiver 410, a user input unit 420, a display 430, a memory 440, and a controller 450.

The receiver 410 is configured to receive a signal or various pieces of data from the outside, and may, for example, include a high-definition multimedia interface (HDMI) connector and a D-sub connector for connection with external devices, or a communication module for connection with a wired/wireless network such as the Internet. The receiver 410 transmits and receives various pieces of information from the medical imaging apparatus 100, the surgical robot 200, and the tracking apparatus 300. For example, the receiver 410 may receive an image taken by the medical imaging apparatus 100, and information about various robot states detected from the surgical robot 200, and may receive information about the positions and poses of the surgical robot 200 and the surgical site tracked by the tracking apparatus 300.

The user input unit 420 is configured to receive various inputs of a user during the spinal surgery planning and the surgical operation and transmit the received inputs to the controller 450 to be described later, and may include various input devices such as a keyboard, a mouse, and a button.

The display 430 is configured to display various pieces of information, which includes an image, graphics, etc., on a screen, and may include a liquid crystal display (LCD) panel, a light emitting diode (LED) panel, an organic light emitting diode (OLED) panel, etc. Further, the user input unit 420 and the display 430 may be integrated and implemented as a single device like a touch screen. The display 430 displays a spinal image, a planning image for setting the insertion position and path of the spinal prostheses, etc. while the robotic surgery is performed.

The user input unit 420 and the display 430 may be configured as physically separated from other elements. For example, the receiver 410, the memory 440, and the controller 450 may be implemented as integrated into the main body of the surgical robot 200, and the user input unit 420 and the display 430 may be implemented as separate devices connected to and communicating with the tracking apparatus 300 and the surgical robot 200.

The memory 440 may be implemented as a memory device such as a random-access memory (RAM), and may be configured to store various operating systems (OS), middleware, platforms, and various applications for the spinal surgery planning apparatus 400, and store program codes, processed video and audio signals, and various pieces of data. Further, the memory 440 may be configured to store a patient's 2D spinal image taken by the medical imaging apparatus 100, a library used during the spinal surgery planning, insertion reference information about the spinal prostheses, etc.

The controller 450 controls overall operations of the spinal surgery planning apparatus 400 based on a user input received through the user input unit 420 or an internal program. The controller 450 may include a program code for processing and controlling a signal, and the processor for executing a program. The controller 450 provides a planning function for registering an image space of a spinal image to a surgical space where a patient's spinal surgery is performed, and setting the insertion position and path of the spinal prostheses, based on the 2D spinal image received through the receiver 410 and the position/pose information of the optical markers received from the tracking apparatus 300.

Referring to FIG. 2, the controller 450 includes a registrator 451, a figure generator 453, a figure adjuster 455, a 3D view generator 457, and a planner 459. For convenience of description, the controller 450 is functionally divided into sub elements. However, the controller 450 may be implemented by software programs made with instructions for carrying out the functions of the sub elements, i.e., the registrator 451, the figure generator 453, the figure adjuster 455, the 3D view generator 457, and the planner 459, and a processor for running the software programs.

The registrator 451 calculates a registration relationship between image space coordinates and surgical space coordinates by registering the image space for the spinal image taken by the medical imaging apparatus 100 and the surgical space where a patient's spinal surgery is performed. In this case, the registrator 451 may register a plurality of 2D images, for example, AP images and LL images, taken in different directions of a patient to a 3D surgical space. For reference, the image space is defined with respect to an image coordinate system, and the surgical space is defined with respect to the coordinate system of the surgical space, in which the coordinate system of the surgical space may be defined based on the makers in the surgical space, for example, the markers attached to a patient's surgical site or the like and detected by the tracking apparatus 300.

The registrator 451 may register the coordinate systems of the surgical space and the image space based on various known registration algorithms. For example, the registrator 451 calculates the spatial coordinates of the sources and the detector by detecting the markers attached to the X-ray source and the detector through the tracking apparatus 300 to identify an X-ray projection parameter when the 2D spinal image is taken, and perform the registration based on the calculated parameter by calibration for the medical imaging apparatus 100. Thus, the registration of the image space and the surgical space based on the calibration parameter for the medical imaging apparatus 100 is well known to those skilled in the art, and thus detailed descriptions thereof will be omitted for simplicity.

Meanwhile, the registration may be performed by the method disclosed in Korean Patent Publication No. 2019-0028592, submitted to Korean Intellectual Property Office by the present applicant as of Mar. 13, 2019 and titled 'C-ARM MEDICAL IMAGING SYSTEM AND REGISTRATION METHOD OF 2D IMAGE AND 3D SPACE.' In brief, the registrator 451 may perform the registration based on a projection image generated by back-projecting the 2D spinal image taken through the medical imaging apparatus 100 to another plane on the X-ray projection path in which a spatial position is accurately grasped by a warping algorithm. In particular, the above registration method may be useful when it is difficult to identify the positions of the X-ray source and the detector of the medical imaging apparatus 100.

Thus, as a registration result of the registrator 451, it is possible to grasp the matching positions between the space for the plurality of 2D spinal images taken through the medical imaging apparatus 100 and the surgical space.

The figure generator 453 generates a virtual 3D figure in the surgical space, and projects the 3D figure on the spinal image based on the registration relationship calculated by the registrator 451. In this case, the virtual 3D figure may have a column shape such as an elliptic cylinder, a cylinder, and a polygonal prism. The figure generator 453 may generate a 3D figure in a position space corresponding to the center of the spinal image based on the registration relationship calculated by the registrator 451. Further, the figure generator 453 may alternately detect a position of a surgical target vertebra body in the spinal image, and generate a 3D figure in a position space corresponding to the detected vertebra body. The figure generator 453 may generate the virtual 3D figure at a position in the surgical space corresponding to the vertebra body on the 2D spinal image based on the registration relationship calculated through the registrator 451, and project that 3D figure on the spinal image.

In this case, the position detection for the vertebra body may be achieved in such a manner that a user inputs the position of the vertebra body in person through the user input unit 420, or may be automatically achieved by various publicly known image recognition algorithms that analyze the brightness and color of the spinal image, the shape of an image object, etc., and detect a specific portion or area. Further, the position of the vertebra body may be automatically detected by performing machine learning based on labelled spinal image training data, or performing deep learning based on algorithms such as a convolutional neural network (CNN), and a convolutional deep belief network (CDBN).

The figure generator 453 may generate a 3D figure according to arbitrary shapes and sizes, but may generate a 3D figure corresponding to the shape, the size, and the like unique characteristics of the vertebra body recognized in the spinal image based on a library stored in the memory 440. In the library, the size, shape, height, and the like properties of the 3D figure are defined according to the characteristics of the vertebra body or the characteristics of the patient, so that differences among patients in the size, shape, etc. of the vertebra body can be reflected in providing the 3D figure suitable for each corresponding patient. The library may be built up and stored in advance based on standard statistical data according to factors related to the shape, size, height and the like properties of the vertebra body corresponding to the age, gender, height, and the like characteristics of the patient, and the positions of the vertebra body currently undergoing a surgical operation.

The figure generator 453 may generate the 3D figure that a user selects in person from the library, or may generate a 3D figure by receiving information about a patient and information about the properties of the vertebra body through the user input unit 420 and selecting the 3D figure in the library based on the received information. Further, the figure generator 453 may recognize the shape, size, etc. of a patient's vertebra body by processing the patient's spinal image based on an image recognition algorithm, and generate a 3D figure suitable for the patient from the library based on a result of the recognition.

The figure generator 453 may generate a 3D figure of which a column type, a column shape, a column height, a size, a radius of a base, a ratio between a major axis and a minor axis of an ellipse, etc. are varied depending on specific shapes of the vertebra body, the position of the surgical target vertebra body, and the characteristics of the patient. For example, when a patient is young or short, and when the vertebra body of that patient is slightly smaller than that corresponding to the statistical data, a matching 3D figure may be generated having a relatively small size or height.

The 3D figure generated by the figure generator 453 and projected on the 2D spinal image is displayed overlapping the spinal image and provided to a user through the display 430.

As described above, the figure generator 453 adaptively selects an initially generated 3D figure according to the characteristics (age, gender, height, etc.) of a patient, the position of a surgical target vertebra body, and the characteristics of the vertebra body, so that a process of adjusting the 3D figure, which will be described later, can be minimized, thereby improving convenience for a user and shortening time taken in the planning.

Figure 3:
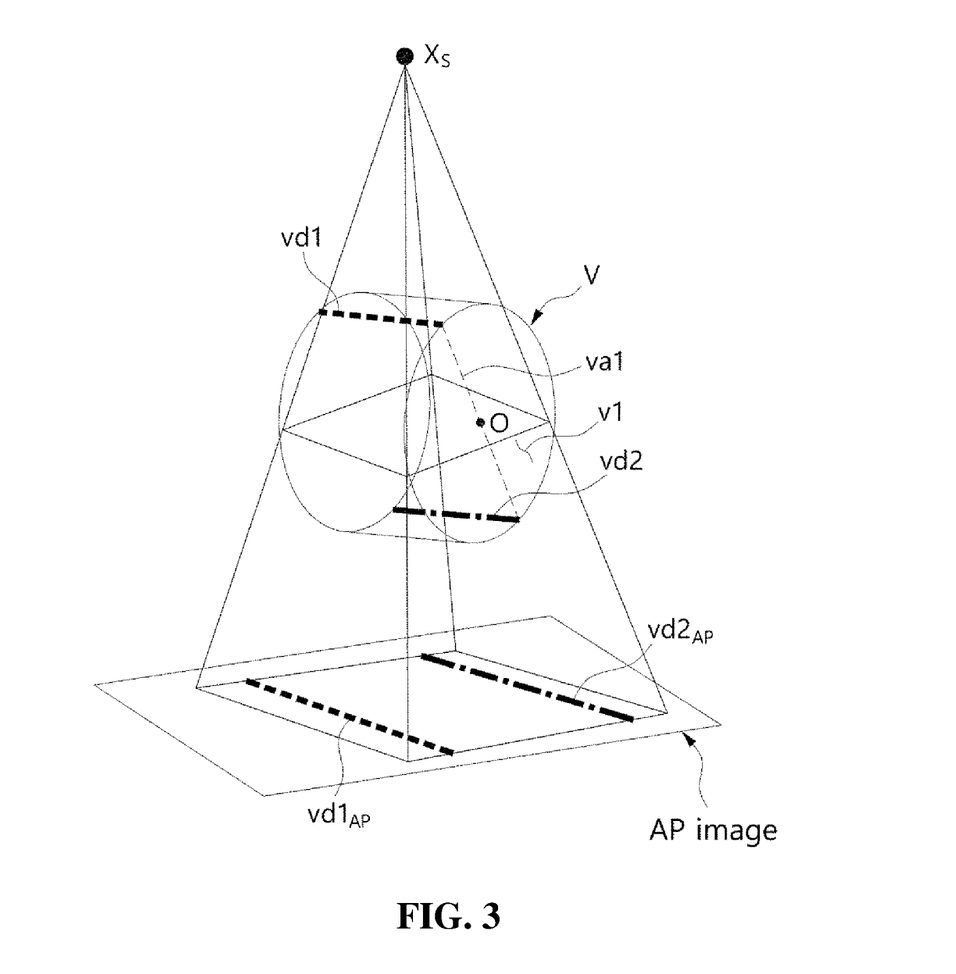
FIGS. 3 and 4 are diagrams illustrating that a virtual three-dimensional (3D) figure generated by a figure generator is projected onto a two-dimensional (2D) spinal image according to an embodiment of the disclosure.
Figure 4:
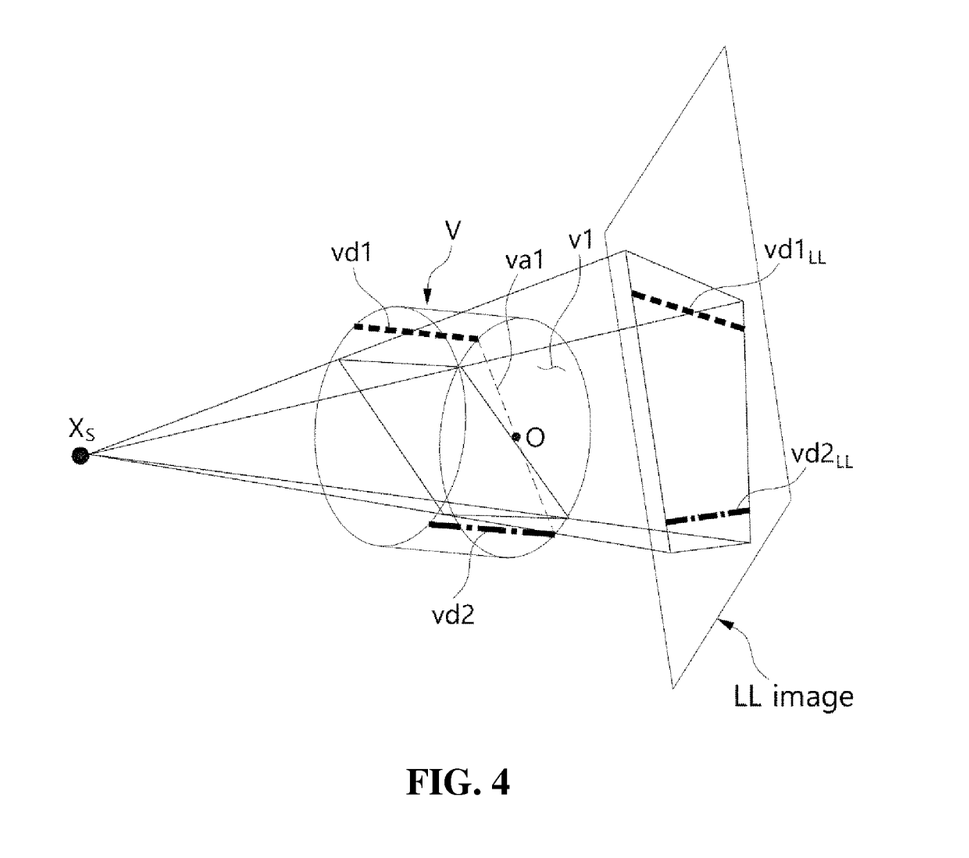

FIGS. 3 and 4 are diagrams illustrating that a virtual 3D figure generated by the figure generator 453 is projected onto a 2D spinal image according to an embodiment of the disclosure.

Referring to FIGS. 3 and 4, FIG. 3 is a diagram of projecting a 3D figure V having an elliptic cylindrical shape onto an AP image, and FIG. 4 is a diagram of projecting the 3D figure V onto an LL image. Here, as a line corresponding to a center line in the superior of a patient's vertebra body, a first line vd1 is a line positioned at an upper end between two lines vd1 and vd2 on a lateral side perpendicular to a first axis va1 on the base v1 passing through the center O of a 3D figure base v1. As a line corresponding to a center line in the inferior of a patient's vertebra body, a second line vd2 is a line positioned at a lower end between the two lines vd1 and vd2 on the lateral side perpendicular to the first axis va1. In this way, vd1 and vd2 are positioned symmetrically to each other with respect to the central axis of the 3D figure.

Meanwhile, in FIG. 3, vd1AP and vd2AP are lines formed by projecting the lines vd1 and vd2 on the lateral side of the 3D figure V onto an AP spinal image, and vd1LL and vd2LL are lines formed by projecting the lines vd1 and vd2 on the lateral side of the 3D figure V onto an LL spinal image. For reference, the positions of vd1AP, vd2AP, vd1LL, and vd2LL on the AP spinal image and the LL spinal image may be varied depending on the specific position of an X-ray source XS of the medical imaging apparatus 100.

The figure adjuster 455 adjusts a 3D figure so that the 3D figure projected on a spinal image (hereinafter referred to as projection figure) can correspond to a predetermined landmark on the spinal image. The figure adjuster 455 may change the shape, size, height, position, etc. of the 3D figure. In this case, the 3D figure may be adjusted based on a user input made through the user input unit 420. To this end, the figure adjuster 455 may generate and provide a control point, which is adjustable by a user, to portions of the 3D figure projected onto the spinal image by the figure generator 453, so that a user can change the shape, size, height, position, etc. of the figure projected and overlappingly displayed onto the spinal image by moving the position of the control point through the mouse, the keyboard, etc. of the user input unit 420.

Figure 5:
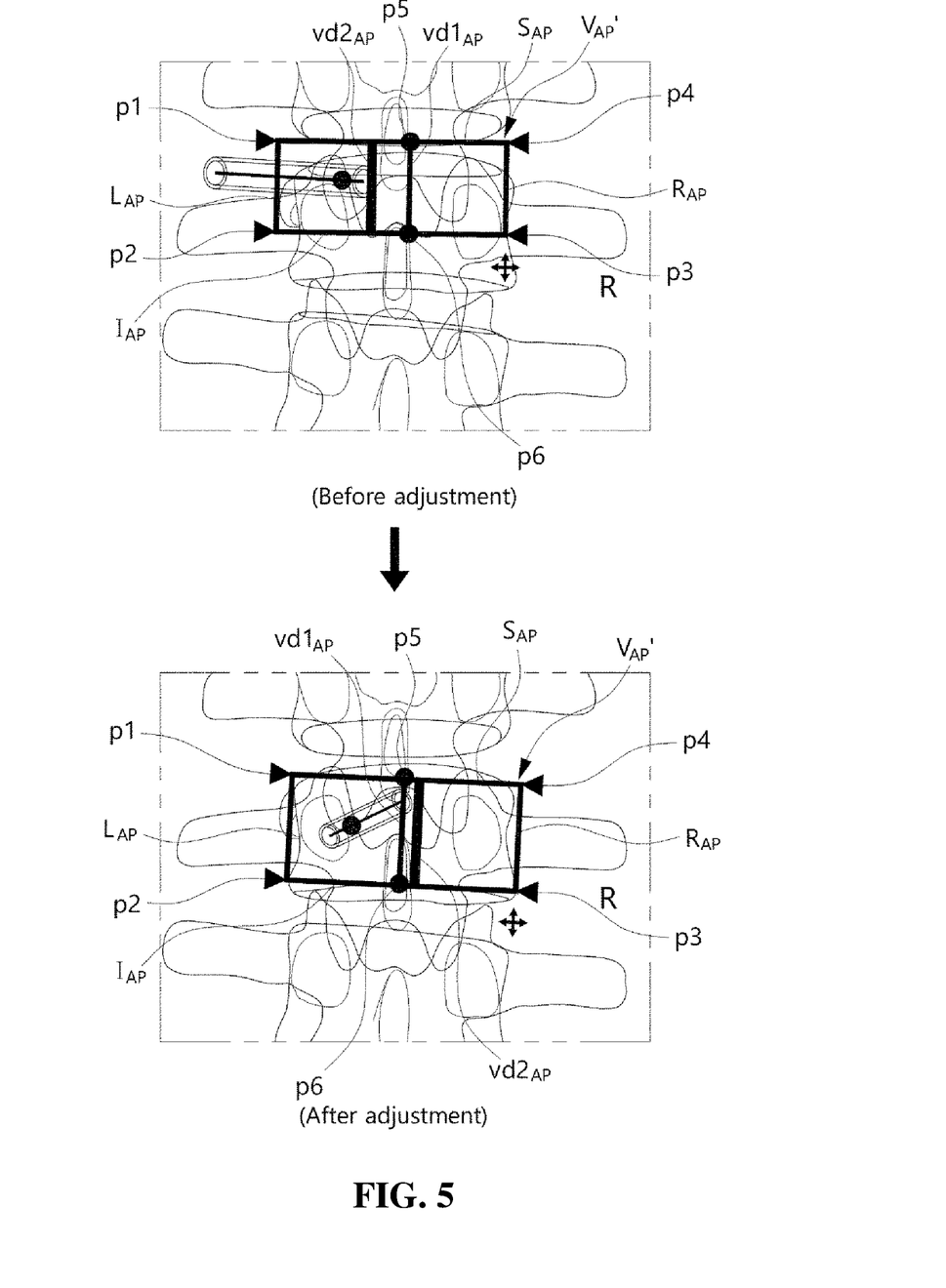
FIGS. 5 and 6 are examples showing that a 3D figure is adjusted by a figure adjuster according to the embodiment of the disclosure.
Figure 6:
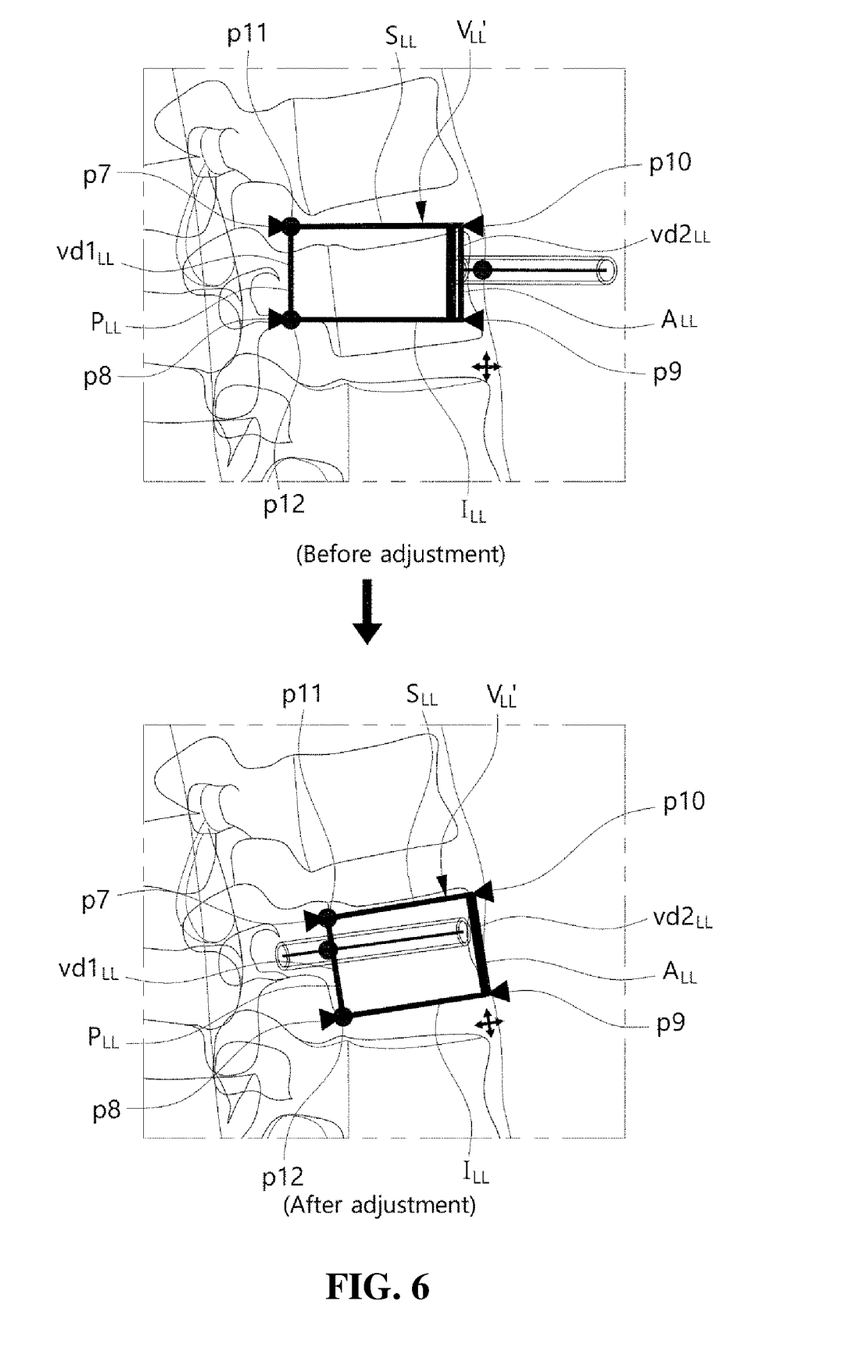

FIGS. 5 and 6 are examples showing that a 3D figure is adjusted by the figure adjuster 455 in response to a user's control using the user input unit 420. For reference, FIG. 5 shows that the 3D figure is adjusted on the AP image, and FIG. 6 shows that the 3D figure is adjusted on the LL image.

Referring to FIG. 5, a projection figure VAP' on the AP spinal image has four sides SAP, IAP, LAP, and RAP, and, as described above, includes the projection lines vd1AP and vd2AP corresponding to two lines vd1 and vd2 on the lateral side of the 3D figure V.

A user may change the position, size, shape, etc. of projection figure VAP' by controlling the control points p1, p2, p3, p4, p5, and p6 provided in the projection figure VAP' through the user input unit 420.

FIG. 5 shows an example that the position and size of the projection figure VAP' are changed on the AP spinal image. For example, a user may adjust the position, size, etc. of the projection figure VAP' so that the boundary of the projection figure VAP', i.e., four sides SAP, IAP, LAP, and RAP can correspond to the boundary of the surgical target vertebra body on the AP spinal image. In this case, the side SAP among four sides is adjusted to correspond to the superior of the vertebra body, the side IAP is adjusted to correspond to the inferior of the vertebra body, the side RAP is adjusted to correspond to the right boundary of the vertebra body, and the side LAP is adjusted to correspond to the left boundary of the vertebra body. In FIG. 5 the projection figure VAP' is misaligned with the vertebra body on the image before the adjustment, but adjusted to correspond to the position and shape of the vertebra body on the image after the adjustment.

At the same time, a user may adjust the projection figure VAP' so that a first projection line vd1AP corresponding to a first lateral side line vd1 of a 3D figure V corresponding to the center line of the superior of the vertebra body can be aligned with the center line of a spinous process on the AP spinal image. In this manner, when the position of the first projection line vd1AP is moved, a position of a second projection line vd2AP positioned symmetrically thereto is also moved.

FIG. 6 shows an example that the position and size of the projection figure VLL' projected on the LL spinal image are changed. Referring to FIG. 6, a projection figure VLL' has four sides PLL, SLL, ALL, and ILL, and includes the projection lines vd1LL and vd2LL corresponding to two lines vd1 and vd2 on the lateral side of the 3D figure V. For reference, in FIG. 6, six lines, i.e., PLL, SLL, ALL, ILL, vd1LL, and vd2LL are all visible to naked eyes before adjustment, but only four lines are visible after adjustment because a first projection line vd1LL overlaps the side PLL to look like one line and the second projection line vd2LL overlaps the side ALL to look like one line. Actually, six lines exist as before the adjustment.

A user may change the position, size, shape, etc. of the projection figure VLL' by adjusting the control points p7, p8, p9, p10, p11 and p12 provided in the projection figure VLL' through the user input unit 420. For example, a user may adjust the projection figure VLL' so that four sides PLL, SLL, ALL, and ILL of the projection figure VLL' can correspond to the boundary of the vertebra body on the LL spinal image. Here, the side SLL among four sides is adjusted to correspond to the superior of the surgical target vertebra body, the side ILL is adjusted to correspond to the inferior of the vertebra body, the side PLL is adjusted to correspond to the posterior boundary of the vertebra body, and the side ALL is adjusted to correspond to the anterior boundary of the vertebra body. Further, the first projection line vd1LL may be adjusted to be aligned with the center line of the spinous process on the LL spinal image. In this case, like that of the AP spinal image, when the position of the first projection line vd1LL is moved on the LL spinal image, a position of a second projection line vd2LL positioned symmetrically thereto will be also moved.

In this way, when a user changes the position, size, shape, etc. of the figure projected on the 2D spinal image such as the AP spinal image and the LL spinal image, the figure adjuster 455 adjusts the position, size, shape, etc. of the 3D figure by equally reflecting the changes of the projected figure in the 3D figure of the surgical space based on a registration result of the registrator 451. Further, when a plurality of 2D spinal images are given, adjustment in a projection figure on one of the spinal images may also be reflected even in the other spinal images based on a registration result. For example, when a user adjusts the projection figure on the AP image, the adjustment of the AP image is also applied to the LL image.

Alternatively, the figure adjuster 455 may be configured to recognize a predetermined landmark on a spinal image based on various well-known image recognition algorithms without the foregoing user input, and automatically adjust the 3D figure so that a specific portion of the 3D figure can be aligned with that landmark. The landmark may be recognized through machine learning or deep learning. Meanwhile, the landmark may include the boundary of the vertebra body, a point on the boundary of the vertebra body, the center line of the spinous process, or a point on the center line of the spinous process. Thus, the projection figure may be automatically adjusted to correspond to the boundary of the vertebra body and the center of the spinous process like the foregoing example where the projection figure is adjusted based on the user input.

In this way, the 3D figure in the surgical space is changed as the projection figure on the 2D spinal image is changed corresponding to the vertebra body, thereby approximating the position, size, shape, etc. of a patient's vertebra body in the surgical space through the 3D figure.

The 3D view generator 457 generates a 3D image for a 3D figure based on a registration result of the registrator 451, and provides the view of the 3D image, which is transformable according to a user's control using the user input unit 420. The generated 3D image is displayed on the display 430.

The 3D view generator 457 may generate a 3D image after completely adjusting the figure through the figure adjuster 455, but may generate and provide a 3D image immediately after the 3D figure is generated by the figure generator 453 so that a user can visually and directly check changes through the 3D view while adjusting the 3D figure. In this case, changes in the projection figure on the 2D spinal image may be reflected in the 3D figure on the 3D image in real time based on the registration relationship calculated by the registrator 451.

Figure 7:
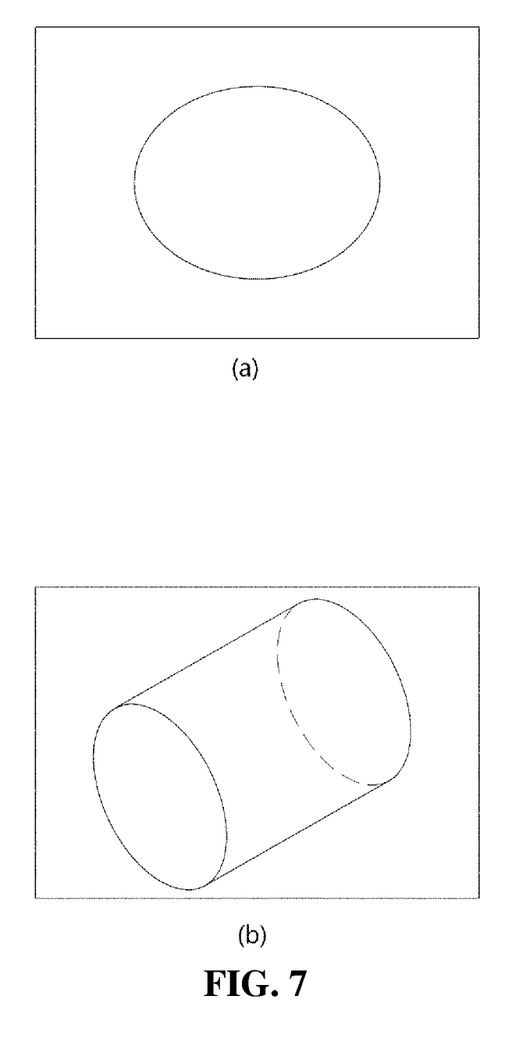
FIG. 7 shows an example of a 3D image generated by a 3D view generator according to an embodiment of the disclosure.

FIG. 7 shows an example of a 3D image generated by the 3D view generator 457 according to an embodiment of the disclosure, in which it is assumed that a 3D figure is an elliptic cylinder.

Referring to FIG. 7, (a) in FIG. 7 shows an axial view image according to an axial direction, and (b) shows a 3D image deviated from the axial direction. This example shows the view of the 3D image, which is freely transformable by a user through the user input unit 420.

The planner 459 is configured to make a surgical plan for the length, diameter, size, insertion position, insertion direction, insertion angle, insertion path, insertion depth, etc. of a spinal prosthesis based on the spinal image and the 3D figure. In this case, a pedicle screw may be used as the spinal prosthesis. However, the spinal prosthesis may include various prostheses inserted in and fixed to a spine during spinal surgery, as well as the pedicle screw. Below, the pedicle screw will be described as an example of the spinal prosthesis.

The planner 459 may first set a reference feature point or position on a spinal image before setting the specific insertion position, direction, angle, path and the like of the spinal prosthesis. For example, when the pedicle screw is inserted, a pivot point may be set as a reference point for inserting the spinal prosthesis at a position corresponding to the center of a pedicle on the spinal image. In this case, a user may input the pivot point in person through a user input unit 420 in consideration of the 3D figure approximating the vertebra body through the 2D spinal image and the 3D image provided by the 3D view generator 457, the shape of the pedicle, etc., or the planner 459 may automatically recognize the pivot point on the spinal image based on a previously trained learning model such as machine learning or deep learning.

The planner 459 may establish a surgical plan for the spinal prosthesis based on a user input and a reference point set like the foregoing pivot point and used as a reference for inserting the spinal prosthesis. To this end, the planner 459 may generate and provide a virtual spinal prosthesis as displayed overlapping the 2D spinal image and the 3D image for the 3D figure through the display 430, and a user may control the insertion position, angle or direction of the virtual spinal prosthesis through the user input unit 420. In this case, the planner 459 may limit the movable range of the virtual spinal prosthesis to pivot around the pivot point, and ensure that the insertion path of the spinal prosthesis or its extension line passes through the pivot point even when a user moves the position or angle of the spinal prosthesis through the user input unit 420.

For the planning, a user may use a plurality of spinal images different in view, such as an AP image and an LL image, and a 3D image for a 3D figure generated by the 3D view generator 457. When a user changes the position, angle or the like of the spinal prosthesis on one among the plurality of images, the planner 459 controls the corresponding change to be commonly reflected in the spinal images and 3D images of other views based on the registration relationship calculated by the registrator 451. As above, multiple view images are interconnected, so that a user can establish a surgical plan without repeating the changes for each view image.

The planner 459 may set criteria for position and angle limits of a spinal prosthesis in advance with respect to a 3D figure approximating a vertebra body, thereby providing a warning message when a user changes the position or angle of the virtual spinal prosthesis beyond the position or angle based on those criteria, or restricting the change not to be made beyond the set criteria.

Figure 8:
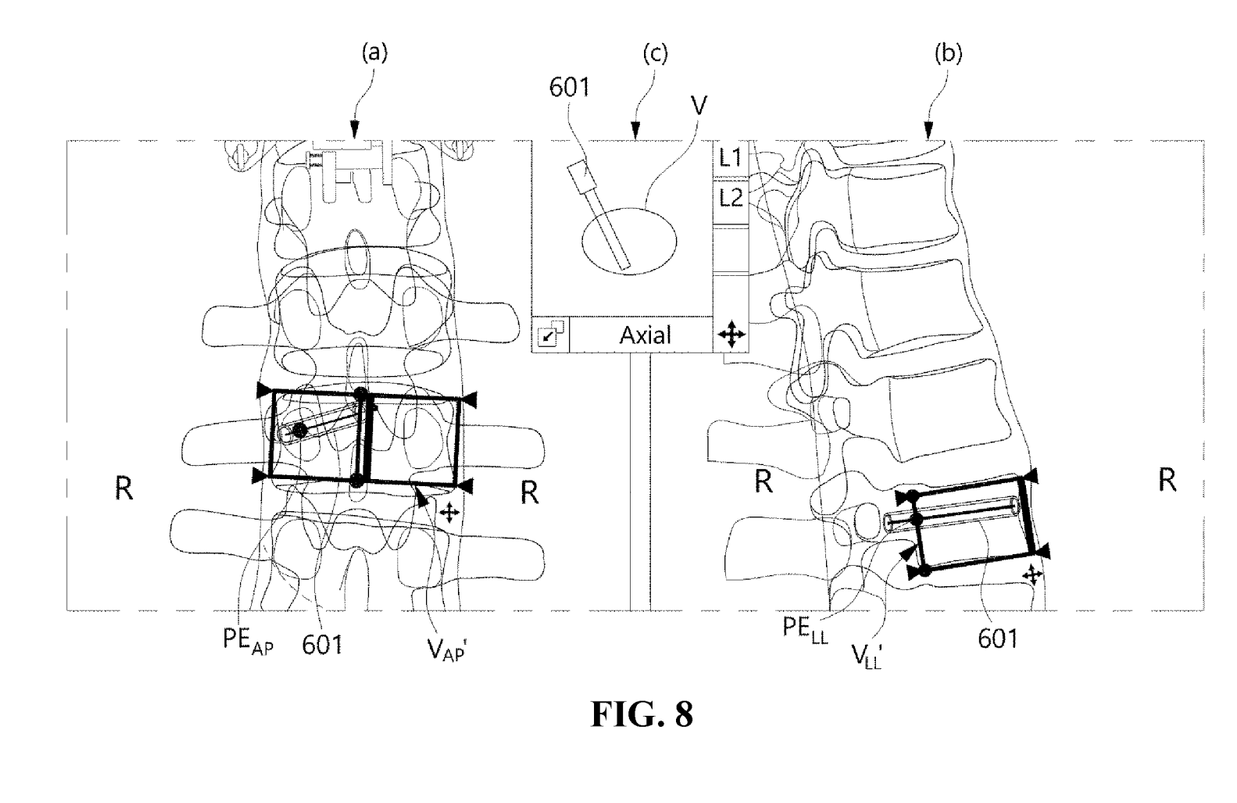
FIG. 8 shows an example of a screen provided through a display during a planning process of a planner according to the embodiment of the disclosure.

FIG. 8 shows an example of a screen provided through the display 430 during the planning process of the planner 459 according to the embodiment of the disclosure.

Referring to FIG. 8, an AP spinal image (a) is displayed on the left side of a screen, an LL spinal image (b) is displayed on the right side of the screen, and a 3D image (c) for a 3D figure is displayed in an upper middle between the two images (a) and (b). Projection figures VAP' and VLL' may be displayed with colors such as green and red different from that of the vertebra body while overlapping the 2D spinal images (a) and (b). Alternatively, the projection figures VAP' and VLL' may be displayed with different saturation or brightness, based on light gray or the like, not to obstruct the vertebra body during the planning process. Of course, the projection figures VAP' and VLL' may not be displayed on the spinal images according to a user's selection or setting.

As shown in FIG. 8, it is possible to take the planning while checking the insertion position, path and the like of the spinal prosthesis in the 2D spinal image and the 3D image based on different views through the display 430, thereby improving convenience for a user and promoting accurate planning.

When a user changes the position, angle, etc. of a virtual spinal prosthesis 601 in one among three images (a), (b) and (c) through the user input unit 420, the planner 459 interconnects three images so that the corresponding change can be applied to all the images. In this case, as described above, the planner 459 uses set pivot points PEAP and PELL as pivotal centers, makes the spinal prosthesis 601 pivot around the pivot point, and ensures that the insertion path of the spinal prosthesis 601 or its extension line passes through the pivot point, thereby limiting the allowable ranges of the insertion position, movement, insertion path, etc. of the spinal prosthesis 601.

Meanwhile, the planner 459 may recognize a specific area or position of a spine on the spinal image through image recognition using various image recognition algorithms, machine learning, and deep learning without relying only on a user input as described above, automatically insert a virtual spinal prosthesis based on insertion criteria stored in advance or previously set by a user, and displays the inserted virtual spinal prosthesis through the display 430.

For example, as shown in FIG. 8, when the insertion position of a pedicle screw 601 is selected, the planner 459 may make the insertion path of the pedicle screw 601 or its extension line be positioned to pass through the pivot points PEAP and PELL and at the same time automatically insert the pedicle screw 601 based on a preset insertion angle.

Besides the insertion position and angle of the pedicle screw, the diameter, length, etc. of the pedicle screw may be selected based on criteria stored in advance or previously set by a user. To this end, the memory 440 may previously store appropriate diameters, lengths or the like reference specifications or products for the spinal prosthesis corresponding to the shape, size, length of the 3D figure, surgical target spinal position, and select the specification or product for the virtual prosthesis suitable for the adjusted 3D figure. For example, when the 3D figure is long or big, a prosthesis having a relatively large length or diameter may be selected as the virtual prosthesis. The planner 459 may give a user an opportunity to modify the position, angle, length, diameter, etc. of the virtual spinal prosthesis automatically inserted.

Figure 9:
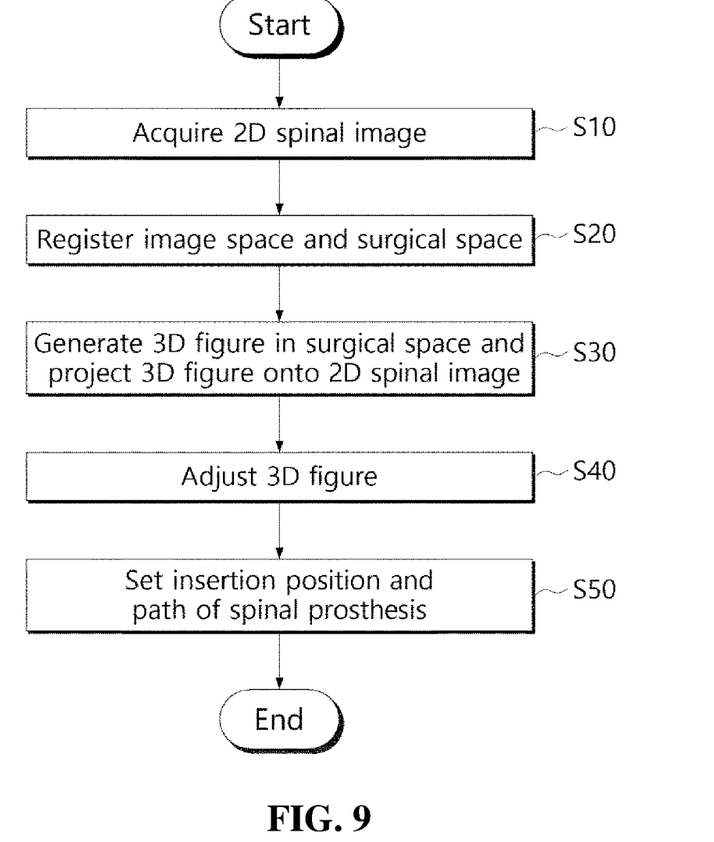
FIG. 9 is a flowchart showing a spinal surgery planning method according to the embodiment of the disclosure.

FIG. 9 is a flowchart showing a spinal surgery planning method according to an embodiment of the disclosure. Below, organic operations between the foregoing elements of the spinal surgery planning apparatus 400 will be described. Repetitive descriptions to the foregoing embodiments will be avoided.

Referring to FIG. 9, the spinal surgery planning method according to the embodiment of the disclosure is based on the premise that a patient's 2D spinal image is obtained through the medical imaging apparatus 100 (S10). In this case, a plurality of images different in the direction of view, such as an AP image and an LL image, may be captured as the 2D spinal image.

Then, the registrator 451 registers the image space for the captured 2D spinal image and the surgical space and calculates a registration relationship between coordinates in the image space and coordinates in the surgical space (S20). In this case, as described above, the registration may be performed by the well-known registration method based on the calibration parameter of the medical imaging apparatus 100, or the method disclosed in Korean Patent Publication No. 2019-0028592, submitted to Korean Intellectual Property Office by the present applicant as of Mar. 13, 2019 and titled 'C-ARM MEDICAL IMAGING SYSTEM AND REGISTRATION METHOD OF 2D IMAGE AND 3D SPACE.'

When the registration is completed, the figure generator 453 generates the virtual 3D figure in the surgical space, and projects the 3D figure onto the 2D spinal image based on the registration relationship (S30). The 3D figure may have a column shape. In this case, the 3D figure may be generated according to arbitrary shapes, sizes, and positions. However, the library where the size, shape, height, and the like properties of the 3D figure are defined according to the unique characteristics of a patient's vertebra body or the characteristics of a patient, such as gender and age, a surgical target spine number, and the like may be taken into account to generate the 3D figure customized for the patient.

The figure adjuster 455 adjusts the shape, size, height, position, and the like of the 3D figure so that the 3D figure projected onto the spinal image can correspond to a predetermined landmark on the spinal image (S40). In this case, the 3D figure in the surgical space may be adjusted by changing the shape, size, height, position, and the like of the 3D figure projected on the spinal image based on the registration relationship. Thus, the shape, size, and position of a patient's vertebra body is approximated by the 3D figure.

Then, the planner 459 sets the insertion position, path, and the like of the spinal prosthesis based on the spinal image and the 3D figure approximating the vertebra body (S50). In this case, the 3D image for the 3D figure in the surgical space is provided so that a user can carry out the planning with reference to the 3D image together with the 2D spinal image, thereby having an effect similar to using a CT image.

Meanwhile, the planner 459 may first set a reference point as the reference for inserting the spinal prosthesis based on a user input, a publicly known image recognition algorithm or a learning model as described above, before setting the specific insertion position, path and the like of the spinal prosthesis. The planner 459 may automatically set the insertion position and path of the spinal prosthesis, or limit the allowable range of the insertion position or path based on a user's control using the user input unit 420 to satisfy insertion conditions so that the spinal prosthesis can pivot around the reference point set as above, for example, around the pivot point or the insertion path of the spinal prosthesis or its extension line can pass through the pivot point.

Further, the planner 459 automatically inserts and provides the virtual spinal prosthesis according to positions and angles stored in advance or based on insertion criteria set by a user, thereby improving convenience for a user.

As described above, with the spinal surgery planning apparatus 400 and the spinal surgery planning method according to the disclosure, the 3D image for the 3D figure approximating the size, shape, etc. of a patient's spine is provided together in the planning process, thereby performing the planning based on the 2D spinal image without a CT scan. In this way, it is possible to accurately take the planning while decreasing a patient's radiation exposure and procedure complexity due to CT image registration, thereby effectively replacing a CT image.

Although it has been described above that all elements constituting an embodiment of the disclosure are combined into a single unit or coupled to be operated as a single unit, the disclosure is not necessarily limited to such an embodiment. In other words, at least two elements may be selectively combined and operate without departing from the scope of the disclosure. In addition, each of the elements may be implemented as independent hardware, but some or all of the elements may be selectively combined with each other, so that they can be implemented as a computer program having program modules for executing some or all of the functions combined in one or more pieces of hardware. Codes and code segments forming the computer program can be easily conceived by an ordinarily skilled person in the technical field of the disclosure. Such a computer program may implement the embodiments of the disclosure as being stored in computer readable media, and being read and executed by a computer. The media for the computer program may include magnetic recording media, and optical recording media.

Further, terms, such as "include," "comprise" or "have" mean the presence of a corresponding element unless otherwise specifically described, and should be construed to include one or more other elements without precluding the presence of them. Unless otherwise defined, all the terms including the technical or scientific terms have the same meanings as understood by a person having ordinary knowledge in the art to which the disclosure pertains. General terms that are defined in a dictionary should be construed to have meanings that are consistent in the context of the related art, and will not be interpreted as having an idealistic or excessively formalistic meaning unless otherwise clearly defined in the disclosure.

Although the embodiments of the disclosure have been described for illustrative purposes, it will be appreciated by a person having ordinary knowledge in the art that various modifications and changes can be made without departing from essential characteristics of the disclosure. Accordingly, the embodiments disclosed in the disclosure are merely to not limit but describe the technical spirit of the disclosure, and the technical spirit of the disclosure is not limited by these embodiments. Further, the scope of the disclosure should be construed based on the appended claims, and all of the technical ideas within the scope equivalent to the appended claims should be also construed as being included in the scope of the disclosure.

The invention claimed is:
1. A spinal surgery planning method comprising:
   acquiring, by spinal surgery planning apparatus, a two-dimensional (2D) spinal image of a patient through a medical imaging apparatus;
   calculating, by the spinal surgery planning apparatus, a registration relationship between coordinates in an image space and coordinates in a surgical space by registering the image space for the 2D spinal image and the surgical space where spinal surgery is performed on the patient;
   generating, by the spinal surgery planning apparatus, a virtual three-dimensional (3D) figure having a column shape in the surgical space;
   projecting, by the spinal surgery planning apparatus, the 3D figure onto the 2D spinal image based on the registration relationship, and displaying the projected 3D figure overlapped on the 2D spinal image;
   adjusting, by the spinal surgery planning apparatus, the 3D figure so that the 3D figure can correspond to a predetermined landmark on the 2D spinal image;
   generating and displaying, by the spinal surgery planning apparatus, a 3D image for the 3D figure of the surgical space; and setting, by the spinal surgery planning apparatus, an insertion position and insertion path of a spinal prosthesis based on the 2D spinal image and the 3D figure.

2. The spinal surgery planning method of claim 1, wherein the adjusting the 3D figure comprises adjusting at least one of the shape, size and position of the 3D figure based on a user input for the 3D figure projected on the 2D spinal image.

3. The spinal surgery planning method of claim 1, wherein the setting the insertion position and path of the spinal prostheses is based on a plurality of 2D spinal images respectively corresponding to different view directions.

4. The spinal surgery planning method of claim 3, wherein the plurality of 2D spinal images respectively corresponding to different view directions comprises an anterior-posterior (AP) image and a lateral-lateral (LL) image.

5. The spinal surgery planning method of claim 1, wherein the setting the insertion position and path of the spinal prostheses comprises setting the insertion position and path of the spinal prosthesis based on a user input using a user input unit.

6. The spinal surgery planning method of claim 1, wherein the adjusting the 3D figure comprises adjusting the 3D figure so that a boundary of a figure formed by projecting the 3D figure on the 2D spinal image can correspond to a boundary of a vertebral body on the 2D spinal image.

7. The spinal surgery planning method of claim 1, wherein projection lines of the 3D figure displayed overlapped on the 2D spinal image comprises a first projection line on which a first line, positioned on a lateral side of the 3D figure and corresponding to a center line in a superior of a vertebra body, is projected, and a second projection line on which a second line, positioned on the lateral side of the 3D figure and corresponding to a center line in an inferior of the vertebra body, is projected.

8. The spinal surgery planning method of claim 7, wherein the adjusting the 3D figure comprises adjusting the 3D figure so that the first projection line can be aligned with a center line of a spinous process on the 2D spinal image.

9. The spinal surgery planning method of claim 1, further comprising setting, by the spinal surgery planning apparatus, a reference point as a reference for inserting the spinal prosthesis on the 2D spinal image, wherein the setting the insertion position and path of the spinal prosthesis comprises limiting an allowable range of the insertion position or insertion path of the spinal prosthesis based on the reference point.

10. The spinal surgery planning method of claim 1, wherein the generating the 3D figure comprises detecting a position of a vertebra body on the 2D spinal image, and generating the 3D figure at the detected position corresponding to the vertebra body.

11. The spinal surgery planning method of claim 1, wherein the generating the 3D figure comprises generating the 3D figure corresponding to characteristics of a vertebra body recognized in the 2D spinal image, based on a library where at least one property among the size, shape and height of the 3D figure is defined according to the characteristics of the vertebra body.

12. A spinal surgery planning apparatus comprising:
a memory configured to store a patient's two-dimensional (2D) spinal image taken by a medical imaging apparatus;
a registrator configured to calculate a registration relationship between coordinates in an image space and coordinates in a surgical space by registering the image space for the 2D spinal image and the surgical space where spinal surgery is performed on the patient;
a figure generator configured to generate a virtual three-dimensional (3D) figure having a column shape in the surgical space and project the 3D figure onto the 2D spinal image based on the registration relationship;
a 3D view generator configured to generate a 3D image for the 3D figure of the surgical space;
a figure adjuster configured to adjust the 3D figure so that the projected 3D figure can correspond to a predetermined landmark on the 2D spinal image;
a display configured to display the projected 3D figure overlapped on the 2D spinal image and display the 3D image for the 3D figure; and
a planner configured to set an insertion position and insertion path of a spinal prosthesis based on the 2D spinal image and the 3D figure.

13. The spinal surgery planning apparatus of claim 12, wherein the 3D image for the 3D figure comprises an axial view image.

14. The spinal surgery planning apparatus of claim 12, wherein the planner controls a change in the spinal prosthesis on one of the 2D spinal image and the 3D image for the 3D figure to be reflected in each other based on the registration relationship.

* * * * *